United States Patent
Gibson et al.

(10) Patent No.: US 11,154,661 B2
(45) Date of Patent: Oct. 26, 2021

(54) AUTO-INJECTOR WITH SIGNALING ELECTRONICS

(71) Applicant: AMGEN INC., Thousand Oaks, CA (US)

(72) Inventors: Scott Robert Gibson, Granada Hills, CA (US); Donald Busby, Thousand Oaks, CA (US); Adam B. McCullough, Westlake Village, CA (US); Peter V. Shultz, Woodland Hills, CA (US); Jimmie L. Ward, Golden, CO (US); Huaying Yang, Vernon Hills, IL (US); Desheng Yin, Thousand Oaks, CA (US); Steven William Badelt, Los Angeles, CA (US); Christopher R. Folk, San Diego, CA (US); Keith P. Kogler, Simi Valley, CA (US); Mark Ka Lai Lee, Newbury Park, CA (US); Ferry Tamtoro, San Ramon, CA (US)

(73) Assignee: AMGEN INC., Thousand Oaks, CA (US)

(*) Notice: Subject to any disclaimer, the term of this patent is extended or adjusted under 35 U.S.C. 154(b) by 533 days.

(21) Appl. No.: 16/060,555

(22) PCT Filed: Jan. 4, 2017

(86) PCT No.: PCT/US2017/012110
§ 371 (c)(1),
(2) Date: Jun. 8, 2018

(87) PCT Pub. No.: WO2017/120178
PCT Pub. Date: Jul. 13, 2017

(65) Prior Publication Data
US 2020/0261657 A1    Aug. 20, 2020

Related U.S. Application Data

(60) Provisional application No. 62/275,491, filed on Jan. 6, 2016.

(51) Int. Cl.
*A61M 5/315* (2006.01)
*A61M 5/20* (2006.01)

(52) U.S. Cl.
CPC .......... *A61M 5/31571* (2013.01); *A61M 5/20* (2013.01); *A61M 2005/2073* (2013.01);
(Continued)

(58) Field of Classification Search
None
See application file for complete search history.

(56) References Cited

U.S. PATENT DOCUMENTS

2008/0269689 A1* 10/2008 Edwards ................. A61M 5/31
604/189
2018/0318526 A1* 11/2018 Yang .................. C07K 16/2803

FOREIGN PATENT DOCUMENTS

CA        2949846 A1     12/2015
WO    WO-2008091838 A2    7/2008
(Continued)

OTHER PUBLICATIONS

International Search Report and Written Opinion for International Application No. PCT/US2017/012110, dated May 9, 2017.

*Primary Examiner* — Jenna Zhang
(74) *Attorney, Agent, or Firm* — Marshall, Gerstein & Borun LLP

(57) ABSTRACT

A drug delivery device includes a housing defining a shell comprising a front portion and a rear portion slidably coupled to the front portion, a drug delivery assembly at least partially disposed within the housing, at least one electronic component, a power source which powers the electronic component, and a switch assembly. The switch assembly is adapted to selectively cause the power source to provide power to the at least one electronic component.

18 Claims, 5 Drawing Sheets

(52) U.S. Cl.
CPC .............. *A61M 2005/31588* (2013.01); *A61M 2205/50* (2013.01); *A61M 2205/8212* (2013.01)

(56) References Cited

FOREIGN PATENT DOCUMENTS

| WO | WO-2010052275 A2 | * | 5/2010 | ........ A61M 5/31551 |
| WO | WO-2010128493 A2 | | 11/2010 | |
| WO | WO-2015136564 A1 | | 9/2015 | |
| WO | WO-2015187793 A1 | * | 12/2015 | .............. A61M 5/20 |

* cited by examiner

AUTO-INJECTOR WITH SIGNALING ELECTRONICS

CROSS-REFERENCE TO RELATED APPLICATIONS

This is the United States national phase of International Patent Application No. PCT/US2017/012110, filed Jan. 4, 2017, which claims the priority benefit of U.S. Provisional Application No. 62/275,491, filed Jan. 6, 2016, the entire contents of each of which are incorporated by reference herein.

BACKGROUND

The present disclosure generally concerns systems and methods for use with drug delivery devices and relating to the powering of electronics contained therein which assist patients and provide increased device functionality.

Drugs may be administered through the use of drug delivery devices, such as autoinjectors or on-body injectors or infusers. These devices may replace older delivery systems using a combination of a syringe and a vial of the drug or medicament, or a pre-filled syringe. Autoinjectors and on-body injectors may be used to automate the injection and delivery or administration process, thereby simplifying the process for certain patient groups or sub-groups for which use of the syringe/vial combination or pre-filled syringe systems would be disadvantageous, whether because of physiological or psychological impediments.

Even with the use of drug delivery devices, such as autoinjectors, patients may experience challenges during the initial use of the drug delivery device after they have been prescribed a drug that is delivered or administered through the use of one of these devices. For example, the user may be uncertain as to whether the medication inside the drug delivery device is the medication prescribed for them. Additionally, the user may be uncertain whether the medication has expired and/or whether the injection should be delayed after a drug delivery device has been removed from cold storage, such as in a refrigerator, and if the injection should be delayed, how long it should be delayed. The user may also be uncertain if the actions and their sequence correctly operate the drug delivery device. Even if the correct actions are performed in the correct sequence, the user may be uncertain the drug has been completely delivered, such that the injection is complete. Patients may have any number of additional concerns related to the administration of the drugs.

As a result of these and other uncertainties and concerns patients may have, systems and methods are often provided which include any number of electronic components capable of assisting with the drug administration process. For example, systems and their corresponding approaches may include any number of sensors or devices capable of monitoring the drug delivery device and/or the surrounding environment to determine whether the drug may be comfortably administered as well as communicate information to the user, healthcare providers, and other interested parties. Because of the use of any number of electronics, the device must be capable of providing power at a number of times before, during, and after the drug administration process. Portable power devices such as batteries may have a limited life and thus difficulties may arise when providing power to the delivery devices after extended durations. Further, these devices may potentially overheat sensitive equipment due to prolonged operation, and may damage the medicament when electronics are in operational states for prolonged periods of time.

Prior to administration of the drug, users may remove components designed to protect the user from inadvertently contacting the delivery cannula. In some approaches, upon removing these components, the electronic devices may power on to receive, sense, and/or transmit data. Users may wish to reattach those components for any number of reasons before administering the drug. As a result, the electronic components may use of a portion or all of the power supply before the drug has been administered.

As set forth in more detail below, the present disclosure describes a drug delivery system and approaches embodying advantageous alternatives to existing drug delivery device packaging that may address one or more of the above challenges or needs.

SUMMARY

According to one aspect of the disclosure, a drug delivery device includes a housing defining a shell and comprising a front portion and a rear portion, a drug delivery assembly at least partially disposed within the housing, at least one electronic component at least partially disposed in the rear portion of the housing, a power source which powers the at least one electronic component being at least partially disposed in the rear portion of the housing, and a switch assembly at least partially disposed in the rear portion of the housing. In these examples, the switch assembly is adapted to cause the power source to provide power to the at least one electronic component.

In some approaches, a signaling assembly for an autoinjector is provided and includes a housing defining a housing shell, at least one electronic component at least partially disposed in the housing shell, a power source at least partially disposed in the housing shell, a switch at least partially disposed in the housing shell, and a spring lever at least partially disposed in the housing shell. The switch is movable between an activated position and a deactivated position and is adapted to cause the power source to provide power to the at least one electronic component when in the activated position. At least a portion of the spring lever is movable between at least a first position and a second position. When the spring lever is in the first position, the spring lever urges the switch into the deactivated position thereby restricting the power source from powering the at least one electronic component. When the spring lever is in the second position, the spring lever urges the switch to occupy the activated position thereby causing the power source to provide power to the at least one electronic component.

In some forms, a signaling assembly for an autoinjector may include a housing defining a housing shell, an actuator body being movably coupled to the housing, at least one electronic component coupled to the actuator body, a power source coupled to the actuator body, a switch coupled to the actuator body, and a spring lever coupled to the actuator body. The switch is movable between an activated position and a deactivated position and is adapted to cause the power source to provide power to the at least one electronic component when in the activated position. At least a portion of the spring lever is movable between at least a first position and a second position. When the spring lever is in the first position, the spring lever urges the switch into the deactivated position thereby restricting the power source from powering the at least one electronic component. When the spring lever is in the second position, the spring lever urges the switch to occupy the activated position thereby causing the power source to provide power to the at least one electronic component.

BRIEF DESCRIPTION OF THE DRAWINGS

The above needs are at least partially met through provision of the autoinjector with a signalling cap described in the following detailed description, particularly when studied in conjunction with the drawings, wherein.

Figure 1:
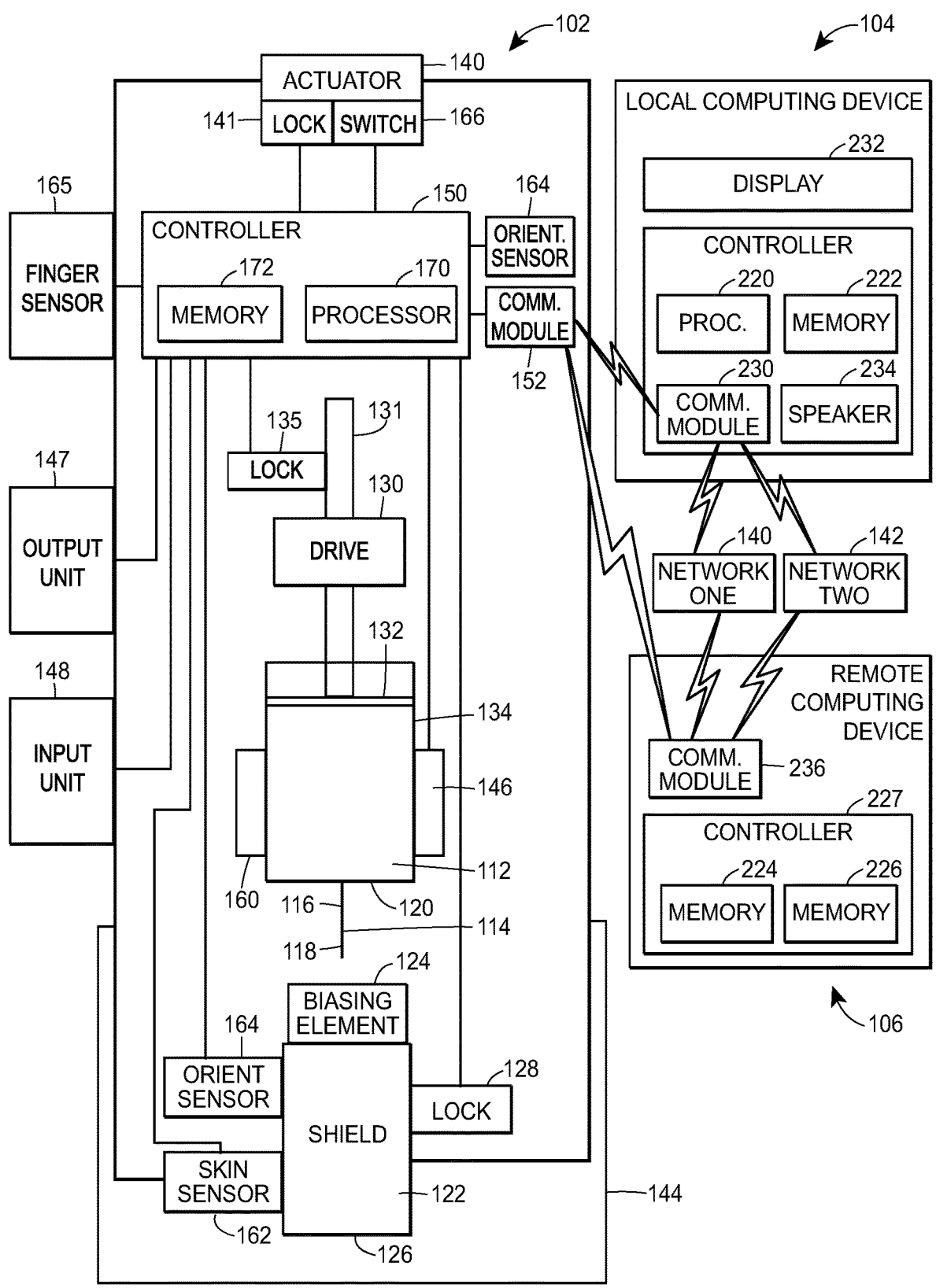
FIG. 1 comprises a schematic illustration of a system including a drug delivery device and a number of computing devices interconnected via a number of communication links and networks in accordance with various embodiments of the invention.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

This application is directed to a plurality of systems and approaches which include a drug delivery device and its corresponding system. In particular, the approaches described herein utilize a switching assembly at least partially disposed within a rear housing which includes any number of electronic components used before, during, and/or after the drug administration process. The assembly includes a mechanism which activates a switch to provide power to the electronics based on the orientation of components of the drug delivery device. By way of example and not by any way of limitation, the mechanism may restrict the electronics from being powered when the assembly has not been actuated and cause the electronics to be powered when the assembly has been actuated. As a result, the assembly may be actuated regardless of whether other components of the drug delivery device have been removed in preparation for administration of the medicament. In these examples, it is possible that a user may initially wish to administer the drug and thus may remove components such as a safety cap, needle shield, and/or a sterile barrier, but may change their mind and decide to delay the administering of the drug until a later time. By dissociating the assembly from the cap or other safety components, the mechanism avoids unnecessary drainage of the battery when the device is in an idle, unused state, and may continue to perform as intended when the administering of the drug or drugs actually occurs. Furthermore, because there are only two possible states (e.g., activated or deactivated), the likelihood of false triggering events is limited. In these forms, particular manufacturing requirements with regard to installation of the cap assembly are also avoided. In other versions, the assembly may be configured to prevent activation until after one or more other components of the drug delivery device have been moved, removed, activated, etc. For example, the assembly may be configured to be activated only after the safety cap, needle shield, and/or sterile barrier are removed.

Generally speaking, pursuant to these various embodiments, a drug delivery device includes a housing defining a shell and comprising a front portion and a rear portion, a drug delivery assembly at least partially disposed within the housing, at least one electronic component at least partially disposed in the rear portion of the housing, a power source which powers the at least one electronic component being at least partially disposed in the rear portion of the housing, and a switch assembly at least partially disposed in the rear portion of the housing. In these examples, the switch assembly is adapted to cause the power source to provide power to the at least one electronic component. The at least one electronic component is adapted to generate data representative of at least one of a condition and an operational state of the drug delivery device. The at least one electronic component may also be adapted to transmit the data to a processing unit.

The switch assembly may further include a switch being at least partially disposed in the rear portion of the housing and being movable between an activated position and a deactivated position and a spring lever having a first portion and a second portion and being at least partially disposed in the rear portion of the housing. At least one of the first portion and the second portion are movable between a first position and a second position. The switch may be adapted to cause the power source to provide power to the at least one electronic component when in the activated position. When the first portion of the spring lever does not engage a portion of the front housing, the spring lever occupies the first position and urges the switch into the deactivated position. When the first portion of the spring lever engages a portion of the front housing, the spring lever occupies the second position and urges the switch into the activated position. In many of these forms, the switch assembly is coupled to the rear portion of the housing such that upon moving the rear portion of the housing to an activated position, the switch assembly causes the power source to provide power to the at least one electronic component.

In some examples, the front portion of the housing comprises a generally cylindrically-shaped component. Similarly, the rear portion of the housing may comprise a generally cylindrically-shaped component. At least a portion of the front portion of the housing is slidably inserted into the rear portion of the housing.

In some forms, the second portion of the spring lever couples to at least one of the at least one electronic component, the power source, and the rear portion of the housing. The rear portion of the housing may comprise any number of protrusions adapted to secure at least one of the at least one electronic component, the power source, and the switch assembly.

In some examples, the first portion of the spring lever may comprise a switch engagement region and an actuation region. When the actuation region experiences a first force, the switch engagement region causes the switch to be positioned in the deactivated position. Further, when the actuation region experiences a second force exerted by the autoinjector, the switch engagement region causes the switch to be positioned in the activated position. In some examples, the first force is less than the second force.

In some approaches, a signaling assembly for an autoinjector is provided and includes a housing defining a housing shell, at least one electronic component at least partially disposed in the housing shell, a power source at least partially disposed in the housing shell, a switch at least partially disposed in the housing shell, and a spring lever at least partially disposed in the housing shell. The switch is movable between an activated position and a deactivated position and is adapted to cause the power source to provide power to the at least one electronic component when in the activated position. At least a portion of the spring lever is movable between at least a first position and a second position. When the spring lever is in the first position, the spring lever urges the switch into the deactivated position thereby restricting the power source from powering the at least one electronic component. When the spring lever is in the second position, the spring lever urges the switch to occupy the activated position thereby causing the power source to provide power to the at least one electronic component.

In some forms, the housing may comprise a front housing and a rear housing being slidably coupled to the front housing. Further, the spring lever may comprise a first length and a second length. The first length may receive a compression force from a portion of the housing. The spring lever is constructed from a metallic material. In some examples, the switch is configured to be biased to the deactivated position when disengaged from the spring lever.

In some forms, a signaling assembly for an autoinjector may include a housing defining a housing shell, an actuator body being movably coupled to the housing, at least one electronic component coupled to the actuator body, a power source coupled to the actuator body, a switch coupled to the actuator body, and a spring lever coupled to the actuator body. The switch is movable between an activated position and a deactivated position and is adapted to cause the power source to provide power to the at least one electronic component when in the activated position. At least a portion of the spring lever is movable between at least a first position and a second position. When the spring lever is in the first position, the spring lever urges the switch into the deactivated position thereby restricting the power source from powering the at least one electronic component. When the spring lever is in the second position, the spring lever urges the switch to occupy the activated position thereby causing the power source to provide power to the at least one electronic component.

In some examples, upon moving the actuator body to an activated position, the switch assembly causes the power source to provide power to the at least one electronic component. The actuator body may comprise a protrusion adapted to secure at least one of the at least one electronic component, the power source, and the switch assembly.

The second portion of the spring lever may include an engagement portion adapted to secure the spring lever to at least one of the at least one electronic component, the power source the switch assembly, and the actuator body. The first portion of the spring lever comprises a switch engagement region and an actuation region. When the actuation region experiences a first force, the switch engagement region causes the switch to be positioned in the deactivated position. When the actuation region experiences a second force exerted by the autoinjector, the switch engagement region causes the switch to be positioned in the activated position. In many of these examples, the first force is less than the second force.

In some examples, the actuator body comprises a button which engages the housing via a housing engagement portion. The housing engagement portion may comprise any number of structures and/or features conventionally used to movably couple and retain structures to each other.

Referring now to the drawings, and in particular to FIG. 1, one generalized example of a system 100 is provided which includes a drug delivery device 102, a local computing device 104 and a remote computing device 106. While the system 100 includes both a local computing device 104 and a remote computing device 106, not all embodiments according to this disclosure include both a local computing device 104 and a remote computing device 106.

The drug delivery device 102 may be in the form of an autoinjector, and thus is adapted for hand-held use and application against the skin of the patient. The drug delivery device 102 includes a housing 110 in which are disposed assemblies or structures that introduce a delivery cannula into the patient, and that eject a drug or medicament from a reservoir 112 through the delivery cannula into the patient. According to certain embodiments, the same assemblies or structures that introduce the delivery cannula into the patient may also eject the drug or medicament from the reservoir through the delivery cannula into the patient. The drug delivery device 102 may also include assemblies or structures that connect the delivery cannula to the reservoir, that withdraw the delivery cannula into the housing 110 through an opening in the housing 110 (not illustrated), or that deploy other structures that will prevent contact with the delivery cannula once the delivery cannula has been removed from the patient. Any number of additional assemblies and structures are possible. The specific embodiment of the drug delivery device 102 discussed below is thus by way of example and not by way of limitation.

Accordingly, the drug delivery device 102 includes a reservoir 112 and a delivery cannula 114 having a first end 116 (e.g., a proximal end) that may be connected or connectable in fluid communication with the reservoir 112 and a second end 118 (e.g., a distal end) that may be inserted into a patient. The delivery cannula 114 may be, for example, a rigid needle having a beveled edge that may be sized such that the second end 118 of the needle 114 is received under the skin so as to deliver a subcutaneous injection of the medicament within the reservoir 112. The first end 116 of the needle 114 may be disposed through a wall 120 of the reservoir 112, and thus be connected in fluid communication with the reservoir 112. Alternatively, the first end 116 of the needle 114 may be disposed only partially through the wall 120 (which wall 120 may be a resalable septum or stopper, for example) such that the first end of the needle 114 may not be connected in fluid communication until the second end 118 of the needle 114 is inserted into the patient. In such a circumstance, the first end 116 of the needle 114 may thus be described as connectable in fluid communication with the reservoir 112, although it will be recognized that there are other mechanisms by which the first end 116 of the needle 114 may be connectable, but not connected, in fluid communication with the reservoir 112.

The drug delivery device 102 includes a shield 122 (e.g., a needle shield) that may be deployed at least after the injection has been completed to limit access to the second end 118 of the needle 114. According to certain embodiments, the shield 122 may have a biasing element 124 (such as a spring) that extends the shield 122 from the housing 110 such that a distal end 126 of the shield 122 extends beyond the second end 118 of the needle 114 except when the shield 122 is disposed against the skin and the insertion of the needle 114 is actuated. In fact, the insertion of the needle 114 may be actuated according to certain embodiments of the drug delivery device 102 by disposing the distal end 126 of the shield 122 on or against the skin of the patient.

The drug delivery device 102 may also include a lock 128 (e.g., a ratchet) that is coupled to the shield 122 and configured to limit or prevent movement of the shield 122 relative to the housing 110 of the drug delivery device 102 such that the distal end 126 of the shield 122 extends from the housing 110 a sufficient distance to limit or prevent contact with the second end 118 of the needle 114, for example, after the needle 114 has been removed or separated from the skin of the patient. In some embodiments, the lock 128 may be coupled to a controller (e.g., controller 150 described in more detail below) which can selectively activate or deactivate the lock 128 based on different types of information regarding the drug delivery device 102, including operational state information, condition information, and/or identity information, in accordance with one or more of the methods described above. When the lock 128 is activated by the controller 150, the lock 128 may be configured to limit or prevent movement of the needle shield 122 relative to the housing 110. When the lock 128 is deactivated by the controller 150, the lock 128 may be configured to allow movement of the needle shield 122 relative to the housing 110.

The drug delivery device 102 also includes at least one drive 130 that may be used to insert the second end 118 of the needle 114 into the skin of the patient, and to eject the drug or medicament from the reservoir 112 through the delivery cannula 114 into the patient. The drive 130 may include one or more springs, according to certain embodiments. According to other embodiments, the drive 130 may include a source of pressurized gas or a source of a material that undergoes a phase change, such that the escaping gas or phase changing material provides a motive force that may be applied to the reservoir 112 to eject the drug therefrom. According to still other embodiments, the drive 130 may include an electromechanical system, such as may include a motor for example, although such an electromechanical system may be more appropriate for the on-body autoinjector or infuser described above. Other embodiments of the drive 130 are also possible.

In one embodiment, the drive 130 may be coupled to a plunger 131 and/or a stopper 132 (e.g., a wall) disposed in the reservoir 112 to move that stopper 132 in a distal direction toward the delivery cannula 114. In accordance with such an embodiment, the stopper 132 may be a stopper that is fixed to a distal end of the plunger 131 and received within a bore 134. The plunger 131, in conjunction with the drive 130, may move the stopper 132 along a longitudinal axis of the drug delivery device 102 through the bore 134 from a proximal end of the bore 134 to a distal end of the bore 134, and thereby eject the medicament from the reservoir 112.

In some embodiments, the drive 130 may also cooperate with the stopper 132 and/or the bore 134 to move the reservoir 112 relative to the housing 110 so as to move the second end 118 of the needle 114 relative to the housing 110 and into the patient. According to those embodiments wherein the drive 130 cooperates with the stopper 132, this may occur before the first end 116 of the needle 114 is in fluid communication with the reservoir 112. According to those embodiments wherein the drive cooperates with the bore 134, the drive may include one component (e.g., first spring) that cooperates with the bore 134 to move the reservoir 112 and needle 114 relative to the housing 110, and a second component (e.g., second spring) that cooperates with the stopper 132 to move the stopper 132 relative to the bore 134.

The drug delivery device 102 may also include a lock 135 that is coupled to the plunger 131 and configured to limit or prevent movement of the plunger 131 relative to the housing 110 of the drug delivery device 102 so that the stopper 132 cannot be advanced to discharge the medicament from the reservoir 112 to the patient. In some embodiments, the lock 135 may be coupled to a controller (e.g., controller 150 described in more detail below) which can selectively activate or deactivate the lock 135 based on different types of information regarding the drug delivery device 102, including operational state information, condition information, and/or identity information, in accordance with one or more of the methods described above. When the lock 135 is activated by the controller 150, the lock 135 may be configured to limit or prevent movement of the plunger 131 relative to the housing 110. When the lock 135 is deactivated by the controller 150, the lock 128 may be configured to allow movement of the plunger 131 relative to the housing 110.

The drive 110 may be associated with an actuator 140. The actuator 140 may activate the drive 130 to cause the drive 130 to insert the needle 114 and eject the drug from the reservoir 112 through the needle 114 into the patient. The actuator 140 may, according to certain embodiments, be the needle shield 122, as explained above. According to other embodiments, such as the one illustrated in FIG. 1, the actuator 140 may be a button that may be manually depressed by the user or patient once the drug delivery device 102 is placed disposed on or against the patient's skin. A lock 141 may be coupled to the actuator 140 and configured to limit or prevent movement of the actuator 140 so that the actuator 140 cannot be used to activate the drive 130. In some embodiments, the lock 141 may be coupled to a controller (e.g., controller 150 described in more detail below) which can selectively activate or deactivate the lock 141 based on different types of information regarding the drug delivery device 102, including operational state information, condition information, and/or identity information, in accordance with one or more of the methods described above. When the lock 141 is activated by the controller 150, the lock 141 may be configured to limit or prevent movement of the actuator 140 relative to the housing 110. When the lock 141 is deactivated by the controller 150, the lock 141 may be configured to allow movement of the actuator 140 relative to the housing 110.

The drug delivery device 102 may also include a removable sterile barrier or signal cap 144 that is disposed about one or more of a distal end of the housing 110, the needle shield 122, and the second end 118 of the delivery cannula 114. The signal cap 144 may be removably attached to the distal end of the housing 110 as shown in FIG. 1. In some embodiments, the signal cap 144 may form an interference or snap fit with the distal end of the housing 110. A frictional force associated with the interference or snap fit may be overcome by manually pulling the signal cap 144 in a direction away from a housing 110. The signal cap 144, when attached to the drug delivery device 102, may reduce the risk of contamination of the delivery cannula 114 and other elements disposed within the drug delivery device 102.

Additionally, the drug delivery device 102 may include a heating element 146 coupled to the exterior of the reservoir 112 and configured to warm the medicament inside the reservoir 112 through, for example, conductive heating. The heating element 146 may be coupled to the controller 150 so that the controller 150 can selectively activate or deactivate the heating element 146 based on different types of information regarding the drug delivery device 102, including operational state information, condition information, and/or identity information, in accordance with one or more of the methods described above. In some embodiments, the heating element 146 may include an electrically conductive coil that is wrapped around the exterior of the reservoir 112. In other embodiments, the heating element may include an electrically conductive coil wrapped around the cannula 114. Alternatively, or additionally, a cooling element (not illustrated) may be coupled to the reservoir 112 and controllable by the controller 150 in a manner similar to the heating element 146.

The drug delivery device 102 may also include an output unit 147 coupled to the housing 110 and configured to notify the patient or user of information related to the drug delivery device 102. The output unit 147 may be coupled to the controller 150 so that the controller 150 can selectively activate or deactivate the output unit 147 based on different types of information regarding the drug delivery device 102, including operational state information, condition information, and/or identity information, in accordance with one or more of the methods described above. The output unit 147 may be any device suitable for conveying information to the patient or user including a display (e.g., a liquid crystal display), a touchscreen, a light (e.g., a light emitting diode), a vibrator (e.g., an electro-mechanical vibrating element), a speaker, and/or an alarm, among other devices.

The drug delivery device 102 may also include an input unit 148 coupled to the housing 110 and configured to allow a user or patient to input information (e.g., password information) to be used by the controller 150. In some embodiments, the input unit 148, the output unit 147, and even the fingerprint sensor 165, may be a single device such as a touchscreen. In other embodiments, the input unit 148 may be a separate device from the output unit 147 such as a keyboard or button.

As illustrated in FIG. 1, the reservoir 112, the biasing element 124, the locks 128, 135, 141, the plunger 131, the stopper 132, and the drive 130, and the heating element 146 are disposed within the housing 110, along with at least part of the delivery cannula 114. Also disposed within the housing 110 is a controller 150, a communication module 152 (e.g., a wireless transmitter), and at least one sensor or switch. According to the embodiment illustrated in FIG. 1, four sensors are included: a temperature sensor 160, a skin sensor 162, at least one orientation sensor 164, and a fingerprint sensor 165. The sensors 160, 162, 164, and 165 may each generate sensor data (e.g., raw or unprocessed data) related to a respective measured property or aspect of the drug delivery device 102. The sensor data may be representative of at least one of a condition or operational state of the drug delivery device 102. Additionally, the drug delivery device 102 includes a switch 166. The controller 150 is coupled to the communication module 152, the locks 128, 135, 141, the sensors 160, 162, 164, 165, the heating element 146, the fingerprint sensor 165, the output unit 147, the input unit 148, and the switch 166. The controller 150 may be configured to process the sensor data generated by the sensors 160, 162, 164, and 165 to determine a condition and/or operational state of the drug delivery device 102. The controller 150, the communication module 152, one or more of the sensors 160, 162, 164, 165 and the switch 166 may be packaged together as a single module, or each component may be fabricated separately and coupled once the components are disposed within the housing 110. According to certain embodiments, each electrical component may be integrated into the structure of the device 102 associated with that electrical component (e.g., the sensors 162 and 164 may be integrated into the shield 122). In some embodiments, the controller 150, the communication module 152, one or more of the sensors 160, 162, 164, 165, and/or the switch 166 may be packaged together inside the signal cap 144.

The controller 150 may include at least one processor 170 (e.g., a microprocessor) and a memory 172 (e.g., a random access memory (RAM), a non-volatile memory such as a hard disk, a flash memory, a removable memory, a non-removable memory, etc.). The controller 150 may also include or be coupled to a power supply, e.g. a battery. The processor 170 may be programmed to carry out the actions that the controller 150 is adapted to perform and the memory 172 may include one or more tangible non-transitory readable memories having executable, computer-readable, non-transitory instructions stored thereon, which instructions when executed by the at least one processor 170 may cause the at least one processor 170 to carry out the actions that the controller 150 is adapted to perform. Alternatively, the controller 150 may include other circuitry that carries out the actions that the controller is adapted to perform.

The memory 172 may store the identity information discussed above. The identity information may be stored in the memory 172 prior to the start of execution of any of the methods discussed above. The identity information may include, by way of example and not by way of limitation, a unique identifier, the name of the drug, the dosage, an expiration date, and information regarding the identity of the patient for whom the drug was prescribed. With this information, the controller 150 or a local computing device (e.g., a smartphone) may make a determination regarding the patient that is about to receive the drug, and provide appropriate informational and/or instructional prompts. As an alternative to memory 172, the identity information may be contained in a QR code label or RFID tag associated with the drug delivery device 102.

The communication module 152 may be any of a number of different communication modules used to communicate with a local computing device (e.g., a smartphone) and/or a remote computing device (e.g., a server operated by the device manufacturer). According to one embodiment, the communication module 152 may be a Bluetooth and/or Bluetooth Low Energy module that is on-board with the controller 150. The communication module 152 is used to transmit information from the drug delivery device 102 to the local computing device 104. Alternatively, other wireless protocols may be used by the communication module 152, such as radio-frequency identification (RFID), Zigbee, Wi-Fi, near field communication (NFC), and others. In fact, the communication may be sent along a hardwired connection, rather than using the electromagnetic (EM) spectrum. As defined herein, a communication transmitted and/or received between the module 152, the local computing device, and/or the remote computing device may be in the form of a hardwired signal or EM signal or a pattern of such signals, for example.

The temperature sensor 160 may be disposed proximate to the reservoir 112 so that the temperature of the drug in the reservoir 112 may be determined. Alternatively, the temperature sensor 160 may simply be disposed in the housing 110, so that an approximate temperature of the drug in the reservoir 112 and of the drug delivery device 102 generally may be determined. According to an embodiment, the temperature sensor 160 may be an on-board temperature sensor 160 attached to the processor 170.

The skin sensor 162 may be attached to or associated with the shield 122 to determine when the drug delivery device 102 is disposed on or against the patient's skin. According to one embodiment, the skin sensor 162 is a pressure sensor. According to other embodiments, the skin sensor 162 may be a capacitance sensor, resistance sensor, or inductance sensor. The skin sensor 162 or the switch 166 (which is attached to or associated with the actuator 140) may be used to determine when the drug delivery device 102 is activated or actuated, depending on the design and operation of the drug delivery device 102 that is used to actuate the drive 130, in accordance with the discussion above. It may also be the case that a signal from the skin sensor 160 is used to determine that the drug delivery device 102 has been activated even when the shield 122 is not used as the actual actuator, the underlying assumption being that the movement of the shield 122 is necessarily related to the actuation of the device 102.

The orientation sensors 164, of which there may be at least two as illustrated, may be associated with the shield 122 (or that portion of the housing 110 adjacent the shield 122) and the controller 150 (which may be, as illustrated, disposed at the other end of the drug delivery device 102 or the housing 110 from the shield 122). The orientation sensors 164 may be magnetometers, for example. In particular, the orientation sensor 164 associated with the controller 150 may be an on-board magnetometer. The orientation sensors 164 may be used to determine the orientation of the drug delivery device 102 (in particular, the housing 110) relative to the injection site (or more particularly, relative to the placement of the drug delivery device 102 on or against the patient's skin).

It will be recognized that the arrangement of the components of the drug delivery device 102 within the housing 110 is but one embodiment of this disclosure. For example, certain components of the drug delivery device 102 may be disposed outside the drug delivery device 102.

According to this embodiment, the drug delivery device 102 may include the housing 110, the reservoir 112, the needle 114, the shield 122, the biasing element 124, the lock 128, the drive 130, and the button 140. Furthermore, the sensors 162, 164 and the switch 166 may be disposed within the housing 110. The fingerprint sensor 165, the output unit 147, and the input unit 148 may be disposed on the exterior of the module 130 so that a user or patient can interact with them.

The separation of the controller 150, communication module 152 and other components into a module may permit the module to be used with multiple instances of the drug delivery device 102. In this regard, the module may be considered to be the reusable portion of the drug delivery device 102/module combination (which may be referred to as the drug delivery device 102 for purposes of this disclosure), while the drug delivery device 102 may be considered to be the disposable portion of the drug delivery device 102. By isolating the more expensive components into the reusable module 400 and the less expensive components (including certain sensors) into the disposable drug delivery device 102, the overall cost of the autoinjector may be optimized. This arrangement of the components in the module and the drug delivery device 102 may also facilitate the manufacture and sterilization of the drug delivery device 102 and module.

The local computing device 104 may be in the form of at least one computing device including at least one processor 220 (e.g., microprocessor) and a memory 222 (e.g., a random access memory (RAM), a non-volatile memory such as a hard disk, a flash memory, a removable memory, a non-removable memory, etc.). The at least one processor 220 and the memory 222 may be incorporated into a controller 223 of the local computing device 104 and/or may be configured separately. Likewise, the remote computing device 106 may be in the form of at least one computing device including at least one processor 224 (e.g., microprocessor) and memory 426 (e.g., a random access memory (RAM), a non-volatile memory such as a hard disk, a flash memory, a removable memory, a non-removable memory, etc.). The at least one processor 224 and the memory 226 may be incorporated into a controller 227 of the local computing device 104 and/or may be configured separately. The memories 222, 226 may include one or more tangible non-transitory computer-readable memories having computer-executable instructions stored thereon (for example, in the form of a custom Mobile Application, or an App for short, or other software module).

According to the illustrated embodiment, the local computing device 104 is a mobile computing device (e.g., a smartphone, smart watch, tablet computer, etc.) while the remote computing device 106 is a server. In some embodiments, the local computing device 104 can include generally any computing device capable of processing data and being synched to and in communication with the drug delivery device 102 such as, for example, a smart wearable device, a personal computer, a laptop computer, a smart television, a smart appliance, a smart automobile, a networked computer, etc. According to other embodiments, the local computing device 104 may be a dedicated device such as a hub or gateway that can establish a communication link with the communication module 152 and potentially the remote computing device 106, where communication with the remote computing device 106 is necessary or desirable.

The local computing device 104 may further include a communication module 230 for wireless communication with the communication module 152 of the drug delivery device 102, for example by using Bluetooth/Bluetooth Low Energy protocol. Alternatively, other wireless protocols may be used by the communication module 152, such as radio-frequency identification (RFID), Zigbee, Wi-Fi, near field communication (NFC), cellular, and others. The local computing device 104 may also include a display 232 to be used to communicate instructions to the user. The local computing device 104 may include other output devices other than the display 232 to communicate with the user, such as a speaker 234 for example. The speaker 234 may be controlled by the processor(s) 220 to provide an audible form of the instructions displayed in written form on the display 232.

The local computing device 104 may also include one or more communication modules, which may be the same as or different from the communication module 230, that may be used to communicate with one or more networks 240, 242. For example, the network 240 may be a wireless radio frequency network, such as a cellular mobile device network, while the network 242 may be a network of computing devices, such as the Internet. The networks 240, 242 may be in communication with each other, such that the local computing device 104 may communicate with the remote computing device 106 over the network 240, the network 242 or a combination of the networks 240, 242. The remote computing device 224 may include a communication module 236 to receive communications from the networks 240, 242.

While the terms "local" and "remote" have been used to describe the local computing device 104 and the remote computing device 106, these terms have not been selected to require a particular spatial or geographical distance between the devices 104, 106. Instead, the terms have been used to suggest a relative proximity to the user, and the fact that the remote computing device 106 is not required to be at the same physical location as the user and the drug delivery device 102. According to certain embodiments, it is possible, even likely, that the remote computing device 106 may be located in a different geographic location than the user and the drug delivery device 102, for example a different city, state or country.

The local computing device 104 and the remote computing device 106 are each separate from, and spaced apart from, the drug delivery device 102 and therefore may each be considered to be an "external computing device" relative to the drug delivery device 102.

Figure 2:
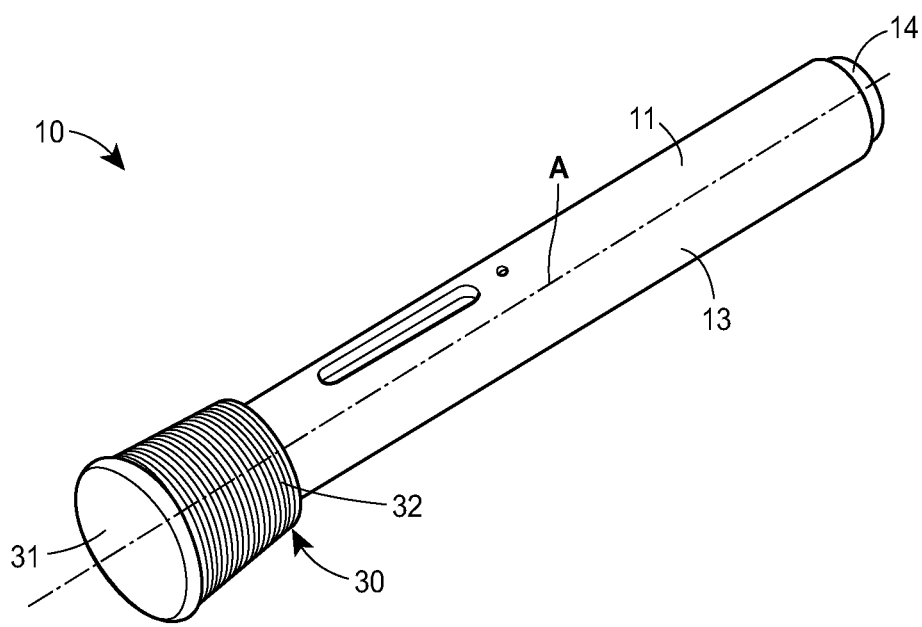
FIG. 2 comprises a perspective view of a drug delivery system in accordance with various embodiments of the invention.
Figure 3:
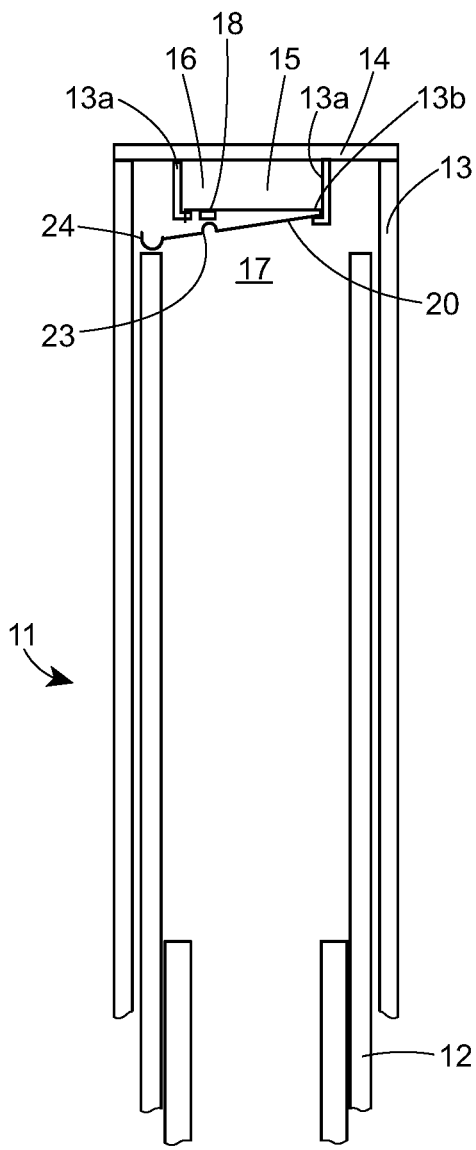
FIG. 3 comprises a cross-sectional view of a drug delivery device assembly illustrating a switch assembly disposed on a surface of a rear housing and being in a deactivated position in accordance with various embodiments of the invention.
Figure 4:
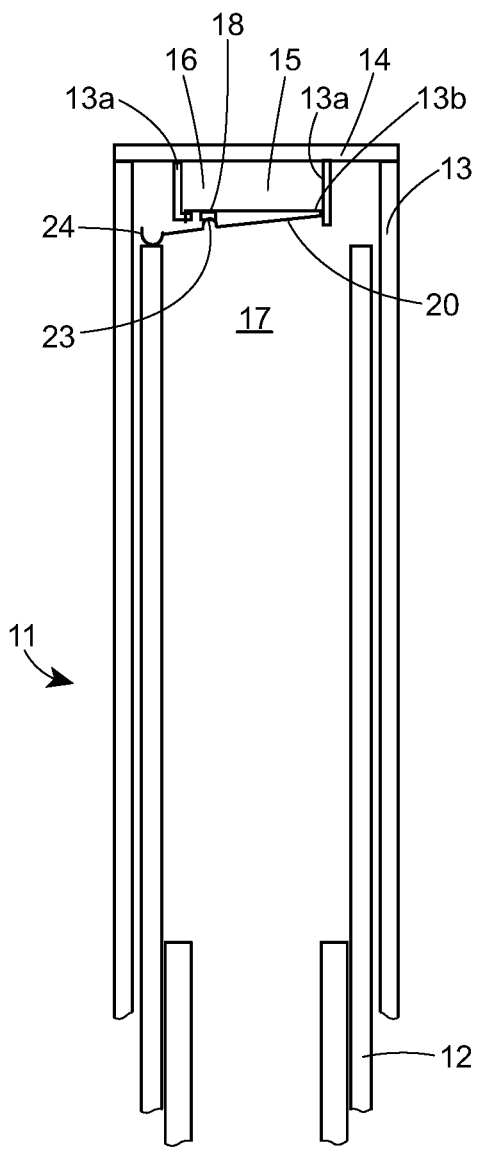
FIG. 4 comprises a cross-sectional view of a drug delivery device assembly illustrating a switch assembly disposed on a surface of a rear housing and being in an activated position in accordance with various embodiments of the invention.

Turning to FIGS. 2-4, a drug delivery device 10 is provided. The drug delivery device 10 may be in the form of an autoinjector, and thus configured for hand-held use and application against the skin of the patient. The drug delivery device 10 may include some or all of the same components as the drug delivery device 102 described above in connection with FIG. 1. The drug delivery device 10 may include a housing 11 defining a shell in which are disposed assemblies or structures such as a drug delivery assembly which introduce a delivery cannula into a patient and that eject a drug or medicament from a reservoir through the delivery cannula into the patient. The housing 11 may include a front portion 12 and a rear portion 13 which are constructed of generally cylindrical, hollow tubes. It is understood that the front portion 12 and the rear portion 13 may be formed in any suitable shape as desired. In some examples, the front portion 12 and the rear portion 13 are slidably coupled to each-other. In these examples, either one of the front portion 12 and the rear portion 13 has an outer diameter that is less than the inner diameter of the other of the front portion 12 and the rear portion 13 such that it may be slidably inserted into the other portion. Either one or both of the front portion 12 and the rear portion 13 may include any number of components to guide or control relative movement therebetween.

The drug delivery device 10 may also include an actuator 14 disposed proximally to the rear portion 13 and configured to be depressed by the patient to activate a drive that causes a plunger to discharge the medicament from the reservoir through the delivery cannula into the patient. The drug delivery device 10 may further include a signal cap 30 (FIG. 2) removably attached to a distal end of the housing 11.

The drug delivery device 10 may also include an electronic component 15, a power source 16, and a switch assembly 17, each of which may be at least partially disposed in the rear portion 13 of the housing 11 (as illustrated in FIG. 3). The power source 16 is used to selectively power the electronic component 15. It is understood that any number of electronic components 15 may be used, and may include any combination of components previously stated with regards to FIG. 1. For example, the controller 150, the memory 172, the processor 170, the communication module 152 (e.g., a Bluetooth module, a Bluetooth Low Energy module, etc.), the skin sensor 162, the orientation sensor 164, the fingerprint sensor 165, the temperature sensor 160, the output unit 147, and/or the input unit 148 may be housed (e.g., embedded) within the rear portion 13 of the housing 11. The electronic component 15 may generate data representative of at least one of a condition and an operational state of the drug delivery device and may further transmit that data to a processing unit.

The cap 30 may serve as a removable sterile barrier which reduces the risk of contamination of the delivery cannula and other elements within the housing 11 prior to use of the drug delivery device 10. As shown in FIG. 2, the cap 30 may be formed by a tubular member 32 and a cover member 31 that covers an open end of the tubular member 32. In some examples, the tubular member 32 and the cover member 31 may be integrally formed as a single unitary structure, or alternatively, formed as separate components which are adhered or mechanically interconnected to each other. The tubular member 32 may be disposed about (e.g., surround) the distal end of the housing 11 and/or a distal end of a delivery cannula (not illustrated), and may removably attach the cap 30 to the housing 11.

In an alternative embodiment, the drug delivery device 10 may include a second removable sterile barrier (not shown), separate from the cap 30, which attaches directly to the reservoir and surrounds the delivery cannula. In such an embodiment, the cap 30 may cover and/or surround the second removable sterile barrier.

Figure 5:
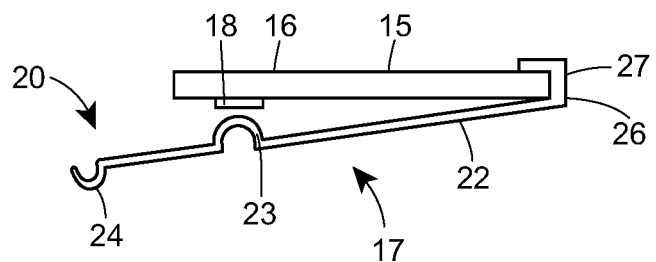
FIG. 5 comprises a cross-sectional view of a switch assembly in accordance with various embodiments of the invention.

Referring back to FIG. 3, the switch assembly 17 selectively causes the power source 16 to provide power to the electronic component 15. The switch assembly 17 may include a switch 18 being movable between an activated position and a deactivated position and a spring lever 20. As shown in FIG. 5, the spring lever 20 can have a first portion 22 and a second portion 26. In some approaches, the first portion 22 is constructed of a flexible material and the second portion 26 is constructed of a rigid material, but otherwise the spring lever 22 can be an integral, one-piece member. In other examples, the spring lever 20 can be constructed of multiple pieces fixed or coupled together. In yet other examples, both the first portion 22 and the second portion 26 are constructed of flexible materials. Both the switch 18 and the spring lever 20 are at least partially disposed within the rear portion 13 of the housing 11. The first portion 22 of the spring lever 20 may include a switch engagement region 23 and an actuation region 24. The second portion 26 of the spring lever 20 may include a coupling region 27.

The engagement region 23 and the actuation region 24 may be generally linear and be constructed from a single piece of material. In some approaches, the first portion 22 may be constructed from any number of individual pieces. The switch engagement region 23 is disposed between the actuation region 24 and the coupling region 27 in the disclosed embodiment. The engagement region 23 may form a bend or protrusion in the first portion 22 in a first direction extending toward the switch 18, and the actuation region 24 may form a bend or protrusion in the first portion 22 in a second direction generally opposite to the bend in the switch engagement region 23. Other examples of configurations of the engagement region 23 and the actuation region 24 are possible.

At least one of the first portion 22 and the second portion 26 of the spring lever 20 is movable between at least a first and second position. In some examples, the spring lever 20 is constructed of a resilient metallic material. Other examples of resilient materials are possible.

The switch 18 is adapted to cause the power source 16 to provide power to the electronic component 15 when in the activated position. The switch 18 may be configured to be biased to the deactivated position when disengaged from the spring lever 20.

As illustrated in FIGS. 3 and 4, the switch assembly 17 may be coupled to the rear portion 13 of the housing 11. Movement of the rear portion 13 to an activated position (e.g., moving the rear portion 13 towards the front portion 12 or vice-versa), may cause the actuation region 24 to engage a rear end surface of the front portion 12, which in turn causes the engagement region 23 to engage the switch 18.

The rear portion 13 of the housing 11 may include any number of extensions 13a having slots 13b to couple to and retain any or all of the electronic component 15, the power source 16, and the switch assembly 17. In some examples, the electronic component 15, the power source 16, and/or the switch assembly 17 may be inserted into the slots 13b to couple to the rear portion 13 of the housing 11. In some examples, the coupling region 27 may include a bend which is dimensioned to "wrap around" a surface of the electronic component 15 and/or the power source 16. In other versions, the coupling portion 27 can be fixed to the rear portion 13 of the housing 11 in other ways. Similarly, the slots 13b may be dimensioned to accept this configuration and provide a secure coupling to the rear portion 13 of the housing. It is understood that the coupling portion 27 may couple to any number of the rear portion 13, the electronic component 15, and/or the power source 16 to provide a secure connection between these components.

In operation and as illustrated in FIG. 3, when the actuation region 24 of the spring lever 20 does not engage a portion of the front housing 12 (e.g., the drug is not being administered and is in an "inactive" state), the spring lever 20 occupies the first position and allows a biasing mechanism (not shown) in the switch 18 to urge the switch 18 into the deactivated position. In some examples, the force exerted on the switch 18 by the spring lever 20 is equal to zero because the spring lever 20 is spaced from the switch 18 when the spring lever 20 occupies the first position.

As illustrated in FIG. 4, when the drug is to be administered, the user moves the rear portion 13 relative to the front portion 14. The actuation region 24 then engages a portion of the front portion 12 and exerts a compressive force thereon, which causes the first portion 22 of the spring lever 20 to move such that the engagement region 23 contacts and causes the switch 18 to move to the activated position. As a result of this compressive force on the spring lever 20, the spring lever 20 occupies the second position and urges the switch 18 into the activated position. In these examples, the force exerted on the switch 18 when the spring lever 20 is in the second position is greater than the force exerted by the spring lever 20 on the switch when the spring lever 20 is in the first position. In other words, the engagement region 23 may be in contact with the switch 18 when the spring 20 is in the first position, but the force exerted on the switch 18 in this first position is insufficient to cause the switch 18 to move to the activated position.

In some embodiments, it may be desirable to minimize and/or eliminate the possibility of the switch 18 becoming deactivated after it has been activated by the lever 20. Such deactivation may inadvertently occur as a result of mechanical relaxation or fatigue. As such, in some versions, the switch 18 could include a latching normally open switch such that upon engagement by the lever 20, the circuit it turned on and will remain on even if the lever 20 disengages the switch 18. Additionally, in some versions, the switch assembly 17 could include a physical latch (not shown) that grasps the lever 20 upon engagement with the switch 18 to maintain contact. Finally, in other versions, the electronic component 15 can include latching circuitry that is activated upon engagement of the lever 20 and switch 18.

Figure 6:
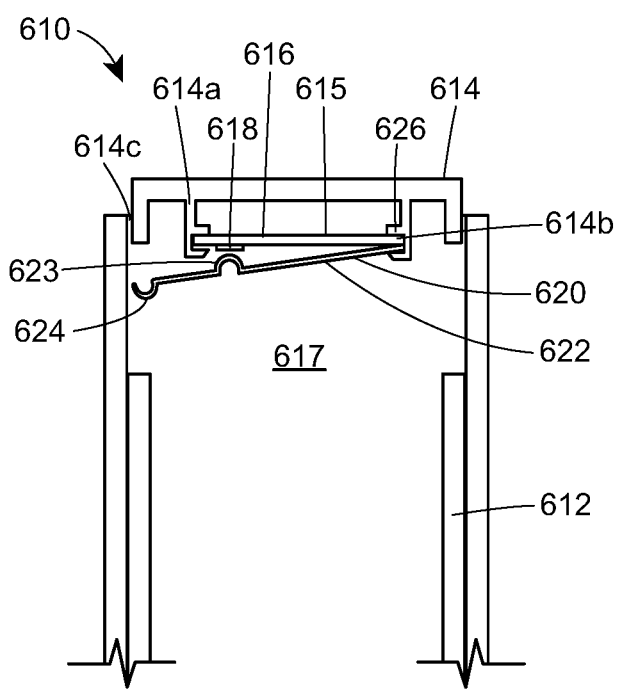
FIG. 6 comprises a cross-sectional view of an alternative switching assembly in accordance with various embodiments of the invention.

Turning to FIG. 6, an alternate signalling assembly 610 is provided. Generally speaking, in this alternate signalling assembly, the actuator body is movable relative to the housing, and components are coupled to the actuator body as opposed to the housing. It is understood that features and/or elements which are similar to those previously described will contain similar two-digit suffixes as those previously provided and, due to similarities in function, will not be fully described for the sake of brevity. For example, the signaling assembly includes a rear portion 613 which bears similarities to the rear portion 13 previously described. The signaling assembly 610 includes a housing defining a housing shell and including a front portion 612 and a rear portion 613, an actuator body 614 being movably coupled to the rear portion 613, at least one electronic component 615 coupled to the actuator body 614, a power source 616 coupled to the actuator body 614, a switch 618 coupled to the actuator body 614, and a spring lever 620 coupled to the actuator body 614. The switch 618 is movable between an activated position and a deactivated position and is adapted to cause the power source 616 to provide power to the electronic component 615 when in the activated position.

The spring lever 620 includes a flexible first portion 622 and a rigid second portion 626. In some embodiments, both the first portion 622 and the second portion 626 are constructed of flexible materials. The first portion 622 of the spring lever 620 may include a switch engagement region 623 and an actuation region 624. The second portion 626 may include a coupling region 627 adapted to couple the spring lever 620 to any number of other components. At least one of the first portion 622 and the second portion 626 is movable between at least a first and second position.

The engagement region 623 and the actuation region 624 may be generally linear and be constructed from a single piece of flexible material. In some approaches, the first portion 622 may be constructed from any number of individual pieces. The switch engagement region 623 is disposed between the actuation region 624 and the coupling region 627 in the disclosed embodiment. The engagement region 623 may form a bend or protrusion in the first portion 622 in a first direction extending toward the switch 618, and the actuation region 624 may form a bend or protrusion in the first portion 622 in a second direction generally opposite to the bend in the switch engagement region 623. Other examples of configurations of the engagement region 623 and the actuation region 624 are possible.

In these embodiments, the actuator body 614 is a separate component from the rear portion 613. The actuator body 614 may be a button which engages the rear portion 613 via a housing engagement portion 614c. The housing engagement portion 614a may include any number of structures and/or features conventionally used to movably couple and retain structures to each other. Other examples are possible. Furthermore, the actuator body 614 may have a resilient member coupled thereto which naturally biases the actuator body 614 in the deactivated position.

As previously described, the actuator body 614 may include any number of extensions 614a having slots 614b to couple any or all of the electronic component 615, the power source 616, the switch 618, and/or the spring lever 620 to be coupled thereto. In some examples, the electronic component 615, the power source 616, the switch 618, and/or the spring lever 620 may be inserted into the slots 614b to couple to the actuator body 614. In some examples, the coupling region 627 may include a bend which is dimensioned to "wrap around" a surface of the electronic component 615 and/or the power source 616. In other versions, the coupling portion 627 can be fixed to the rear portion 613 of the housing in other ways. Similarly, the slots 614b may be dimensioned to accept this configuration and provide a secure coupling to the actuator body 614. It is understood that the coupling portion 627 may couple to any number of the actuator body 614, the electronic component 615, and/or the power source 616 to provide a secure connection between these components.

Generally speaking, when the actuator body 614 is not actuated, the actuation region 624 of the spring 620 experiences a first force, and the switch engagement region 623 causes the switch 618 to be positioned in the deactivated position. When the actuator body 614 is actuated, the actuation region 624 of the spring 620 experiences a second force exerted by the first portion 612 of the housing which causes the first portion 622 to move to a position where the switch engagement region 623 contacts and the switch 628 to the activated position. In these examples, the first force is less than the second force.

When the spring lever 620 is in the first position, the spring lever 620 allows a resilient member in the switch 618 to urge the switch 618 into the deactivated position, thereby restricting the power source 616 from powering the electronic component 615. When the spring lever 620 is in the second position, the spring lever 620 urges the switch 618 to occupy the activated position thereby causing the power source 616 to provide power to the electronic component 615.

So configured, removing and replacing the safety features (e.g., the cap, sterile barrier, etc.) do not effect actuation of the electronics contained in the drug delivery device. Translation of the rear housing (or the actuator body) relative to the front portion of the housing engages the electronics. After the electronics are activated, the front and rear portions of the housing are stabilized in the same position. As a result, replacing the cap will not deactivate the electronics.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

The above description describes various systems and methods for use with a drug delivery device. It should be clear that the system, drug delivery device or methods can further comprise use of a medicament listed below with the caveat that the following list should neither be considered to be all inclusive nor limiting. The medicament will be contained in a reservoir. In some instances, the reservoir is a primary container that is either filled or pre-filled for treatment with the medicament. The primary container can be a cartridge or a pre-filled syringe.

For example, the drug delivery device or more specifically the reservoir of the device may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the drug delivery device may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgrastim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO:2 as set forth therein in FIG. 2 and/or the heavy chain of SEQ ID NO:4, as set forth therein in FIG. 4, each of which is individually and specifically incorporated by reference herein in its entirety fully as disclosed in the foregoing publication;

Myostatin binding proteins, peptibodies, and related proteins, and the like, including myostatin specific peptibodies, particularly those described in U.S. Publication No. 2004/0181033 and PCT Publication No. WO 2004/058988, which are incorporated by reference herein in their entirety particularly in parts pertinent to myostatin specific peptibodies, including but not limited to peptibodies of the mTN8-19 family, including those of SEQ ID NOS:305-351, including TN8-19-1 through TN8-19-40, TN8-19 coni and TN8-19 cont; peptibodies of the mL2 family of SEQ ID NOS:357-383; the mL15 family of SEQ ID NOS:384-409; the mL17 family of SEQ ID NOS:410-438; the mL20 family of SEQ ID NOS:439-446; the mL21 family of SEQ ID NOS:447-452; the mL24 family of SEQ ID NOS:453-454; and those of SEQ ID NOS:615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publication No. 2004/097712, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned publication;

Ang2 specific antibodies, peptibodies, and related proteins, and the like, including but not limited to those described in PCT Publication No. WO 03/057134 and U.S. Publication No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2xL1(N); 2xL1(N) WT; Con4 (N), Con4 (N) 1K WT, 2xCon4 (N) 1K; L1C; L1C 1K; 2xL1C; Con4C; Con4C 1K; 2xCon4C 1K; Con4-L1 (N); Con4-L1C; TN-12-9 (N); C17 (N); TN8-8(N); TN8-14 (N); Con 1 (N), also including anti-Ang 2 antibodies and formulations such as those described in PCT Publication No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; AblA1; AblF; AblK; AblP; and AblP, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in U.S. Publication No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing publication;

Also among non-limiting examples of anti-IGF-1R antibodies for use in the methods and compositions of the present invention are each and all of those described in:

(i) U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

(iii) PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) U.S. Publication No. 2005/0084906 (published Apr. 21, 2005), including but not limited to antibody 7C10, chimaeric antibody C7C10, antibody h7C10, antibody 7H2M, chimaeric antibody*7C10, antibody GM 607, humanized antibody 7C10 version 1, humanized antibody 7C10 version 2, humanized antibody 7C10 version 3, and antibody 7H2HM, as described therein;

(v) U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (γ4), deposited at the ATCC under number PTA-5214, and a light chain encoded by a polynucleotide in plasmid 15H12/19D12 LCF (κ), deposited at the ATCC under number PTA-5220, as described therein; and (viii) U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, which are incorporated herein by reference in their entireties as to such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein), each of which is individually and specifically incorporated by reference herein in its entirety fully as disclosed in the foregoing publication;

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing publication and in Thakur et al. (1999), Mol. Immunol. 36:1107-1115. In addition, description of the properties of these antibodies provided in the foregoing publication is also incorporated by reference herein in its entirety. Specific antibodies include those having the heavy chain of SEQ ID NO:17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in the foregoing publication. A specific antibody contemplated is antibody 1119 as disclosed in the foregoing U.S. publication and having a complete heavy chain of SEQ ID NO:17 as disclosed therein and having a complete light chain of SEQ ID NO:18 as disclosed therein;

TALL-1 specific antibodies, peptibodies, and the related proteins, and the like, and other TALL specific binding proteins, such as those described in U.S. Publication Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and OA-5d5 described in U.S. Pat. Nos. 5,686,292 and 6,468,529 and in PCT Publication No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in U.S. Publication No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publication No. WO 2006/081171, which is herein incorporated by reference in its entirety, particularly in parts pertinent to proteins that bind amyloid-beta proteins. One antibody contemplated is an antibody having a heavy chain variable region comprising SEQ ID NO:8 and a light chain variable region having SEQ ID NO:6 as disclosed in the foregoing publication;

c-Kit specific antibodies, peptibodies, related proteins, and the like, including but not limited to those described in U.S. Publication No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, which is incorporated herein by reference in its entirety, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgastrim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-α4integrin mAb); Valortim® (MDX-1303, anti-B. anthracis protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Rα mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5 β1 integrin mAb); MDX-010 (ipilimumab, anti-CTLA-4 mAb and VEGFR-1 (IMC-18F1); anti-BR3 mAb; anti-C. difficile Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MEDI-1103); anti-IGF1R mAb; anti-IGF-1R mAb (HuMax-Inflam); anti-IL12 mAb (ABT-874); anti-IL12/1L23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGB mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFI3 mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab), as well as molecules, variants, analogs or derivatives thereof as disclosed in the following patents or patent applications, each of which is herein incorporated by reference in its entirety for all purposes: U.S. Pat. No. 8,030,547, U.S. Publication No. 2013/0064825, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223,593 and 7,537,924); OncoVEXGALV/CD (U.S. Pat. No. 7,981,669); OrienX010 (Lei et al. (2013), World J. Gastroenterol., 19:5138-5143); G207, 1716; NV1020; NV12023; NV1034 and NV1042 (Vargehes et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, bispecific T cell engager (BiTE®) antibodies, e.g. BLINCYTO® (blinatumomab), can be used in the device. Alternatively, included can be an APJ large molecule agonist e.g., apelin or analogues thereof in the device. Information relating to such molecules can be found in PCT Publication No. WO 2014/099984.

In certain embodiments, the medicament comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the medicament comprises a therapeutically effective amount of the anti-TSLP antibody designated as A5 within U.S. Pat. No. 7,982,016.

Although the drug injection device, signal cap, systems, methods, and elements thereof, have been described in terms of exemplary embodiments, they are not limited thereto. The detailed description is to be construed as exemplary only and does not describe every possible embodiment of the invention because describing every possible embodiment would be impractical, if not impossible. Numerous alternative embodiments could be implemented, using either current technology or technology developed after the filing date of this patent that would still fall within the scope of the claims defining the invention.

It should be understood that the legal scope of the invention is defined by the words of the claims set forth at the end of this patent. The appended claims should be construed broadly to include other variants and embodiments of same, which may be made by those skilled in the art without departing from the scope and range of equivalents of the device, drive damper mechanisms, systems, methods, and their elements.

What is claimed is:

1. A drug delivery device comprising:
a housing defining a shell, the housing comprising a front portion and a rear portion slidably coupled to the front portion;
a drug delivery assembly at least partially disposed within the housing,
at least one electronic component at least partially disposed in the rear portion of the housing,
a power source at least partially disposed in the rear portion of the housing for selectively powering the at least one electronic component; and
a switch assembly at least partially disposed in the rear portion of the housing, the switch assembly adapted to selectively cause the power source to provide power to the at least one electronic component in response to relative movement between the front portion and the rear portion of the housing, wherein the switch assembly further comprises:
a switch being at least partially disposed in the rear portion of the housing and being movable between an activated position and a deactivated position, the switch being adapted to cause the power source to provide power to the at least one electronic component when in the activated position; and
a spring lever having a first portion and a second portion and being at least partially disposed in the rear portion of the housing, at least one of the first portion and the second portion being movable between at least a first position and a second position; wherein
(a) when the first portion of the spring lever does not engage a portion of the front housing, the spring lever occupies the first position and urges the switch into the deactivated position, and
(b) when the first portion of the spring lever engages the portion of the front housing, the spring lever occupies the second position and urges the switch into the activated position.

2. The drug delivery device of claim 1, wherein the switch assembly is coupled to the rear portion of the housing such that upon moving the rear portion of the housing to an activated position, the switch assembly causes the power source to provide power to the at least one electronic component.

3. The drug delivery device of claim 1, wherein the front portion of the housing comprises a generally cylindrically-shaped component and the rear portion of the housing comprises a generally cylindrically-shaped component, wherein at least the portion of the front portion of the housing is slidably inserted into the rear portion of the housing.

4. The drug delivery device of claim 1, wherein the second portion of the spring lever is coupled to at least one of the at least one electronic component, the power source, and the rear portion of the housing.

5. The drug delivery device of claim 1, wherein the at least one electronic component generates data representative of at least one of a condition and an operational state of the drug delivery device, the at least one electronic component further transmits the data to a processing unit.

6. The drug delivery device of claim 1, wherein the first portion of the spring lever comprises a switch engagement region and an actuation region, wherein
(a) when the actuation region experiences a first force, the switch engagement region causes the switch to be positioned in the deactivated position, and
(b) when the actuation region experiences a second force exerted by the portion of the front housing, the switch engagement region causes the switch to be positioned in the activated position.

7. The drug delivery device of claim 6, wherein the first force is less than the second force.

8. A signaling assembly for an autoinjector comprising:
a housing defining a housing shell;
at least one electronic component at least partially disposed in the housing shell;
a power source at least partially disposed in the housing shell;
a switch at least partially disposed in the housing shell and being movable between an activated position and a deactivated position, the switch being adapted to cause the power source to provide power to the at least one electronic component when in the activated position and is adapted to be biased to the deactivated position when disengaged from the spring lever; and
a spring lever at least partially disposed in the housing shell, at least a portion of the spring lever being movable between at least a first position and a second position; wherein
(a) when at least the portion of the spring lever is in the first position, the spring lever urges the switch into the deactivated position thereby restricting the power source from powering the at least one electronic component, and
(b) when at least the portion of the spring lever is in the second position, the spring lever urges the switch to occupy the activated position thereby causing the power source to provide power to the at least one electronic component.

9. The signaling assembly of claim 8, wherein the housing comprises a front housing and a rear housing slidably coupled to the front housing.

10. The signaling assembly of claim 8, wherein the spring lever further comprises a first portion and a second portion, wherein the first portion receives a compression force from a portion of the housing.

11. The signaling assembly of claim 8, further comprising:
an actuator body being movably coupled to the housing;
the at least one electronic component, the power source, the switch, and the spring lever each being coupled to the actuator body;
the spring lever having a first portion and a second portion, at least one of the first portion and the second portion being movable between at least the first position and the second position in response to the actuator body moving relative to the housing.

12. The signaling assembly of claim 11, wherein upon moving the actuator body to an activated position, the switch causes the power source to provide power to the at least one electronic component.

13. The signaling assembly of claim 11, wherein the second portion of the spring lever includes a coupling portion adapted to secure the spring lever to at least one of the at least one electronic component, the power source, the switch, and the actuator body.

14. The signaling assembly of claim 11, wherein the first portion of the spring lever comprises a switch engagement region and an actuation region, wherein
   (a) when the actuation region experiences a first force, the switch engagement region causes the switch to be positioned in the deactivated position, and
   (b) when the actuation region experiences a second force exerted by the autoinjector, the switch engagement region causes the switch to be positioned in the activated position.

15. The signaling assembly of claim 14, wherein the first force is less than the second force.

16. The signaling assembly of claim 11, wherein the actuator body comprises a button which engages the housing via a housing engagement portion.

17. The signaling assembly of claim 16, wherein the housing engagement portion comprises at least one of:
   (a) a tooth coupling adapted to engage a notch disposed on the housing; and
   (b) a stepped coupling.

18. The signaling assembly of claim 11, wherein the at least one electronic component generates data representative of at least one of a condition and an operational state of the drug delivery device, the at least one electronic component further transmits the data to a processing unit.

* * * * *